United States Patent [19]

Chachques et al.

[11] Patent Number: 4,735,205

[45] Date of Patent: Apr. 5, 1988

[54] METHOD AND APPARATUS INCLUDING A SLIDING INSULATION LEAD FOR CARDIAC ASSISTANCE

[75] Inventors: Juan C. Chachques, Savigny Sur Orge, France; Pierre A. Grandjean, Heerlen; Karel Smits, Oirsbeek, both of Netherlands

[73] Assignee: Medtronic, Inc., Minneapolis, Minn.

[21] Appl. No.: 831,949

[22] Filed: Feb. 24, 1986

[51] Int. Cl.[4] .............................................. A61N 1/36
[52] U.S. Cl. .......................... 128/419 PG; 128/1 D; 128/419 P; 128/785
[58] Field of Search ............... 128/783, 784, 785, 786, 128/419 P, 419 PG, 421, 422, 1 D; 623/3

[56] References Cited

U.S. PATENT DOCUMENTS

| | | | |
|---|---|---|---|
| 452,220 | 5/1891 | Gunning | 128/786 |
| 3,474,791 | 10/1969 | Bentov | 128/785 |
| 3,485,247 | 12/1969 | Ackerman | 128/784 |
| 3,516,412 | 6/1970 | Ackerman | 128/784 |
| 3,949,757 | 4/1976 | Sabel | 128/419 X |
| 4,338,947 | 7/1982 | Williams | 128/785 |
| 4,341,226 | 7/1982 | Peters | 128/784 |
| 4,351,345 | 9/1982 | Carney | 128/786 |
| 4,394,866 | 7/1983 | Hughes | 128/786 |
| 4,411,268 | 10/1983 | Cox | 128/421 |
| 4,444,207 | 4/1984 | Rubicsek | 128/785 |
| 4,516,584 | 5/1985 | Garcia | 128/419 P |

OTHER PUBLICATIONS

"Development of a Nontiring Stimulation of the Latissimus Dorsi Flap to Replace Myocardium", J. C. Chachques, A. Carpentier and S. Chauvaud, Artif. Organs, vol. 8, No. 3, 1984, pp. 379, 380.

"Functional adaption in skeletal muscles", S. Salmons TINS 3:134–137, 1980.

"Experimental cardioplasty using the Latissimus Dorsi muscle flap", Juan C. Chachques, Vladimir Mitz, Marc Hero, Pierre Arhan et al., The Journal of Cardiovascular Surgery, vol. 26-No. 5-pp. 457–462 (Sep.-Oct. 1985).

"Synchronously stimulated skeletal muscle graft for myocardial repair", Michael L. Deward, M.D., Davis C. Drinkwater, M.D., Carin Wittnich, D.V.M. et al., J. Thorac Cardiovasc Surg 87"325–331, 1984.

(List continued on next page.)

*Primary Examiner*—William E. Kamm
*Attorney, Agent, or Firm*—Joseph F. Breimayer; Robert C. Beck; John L. Rooney

[57] ABSTRACT

A method and apparatus for providing muscle stimulation in the field of Function Electrical Stimulation, particularly electrical stimulation to a muscle employed as a myocardial substitute. The Latissimus Dorsi muscular flap is divided into two parts to cover the surfaces of the heart and inserted into a thoracic cavity by means of a segmental resection of the second rib. After or before positioning the muscle in this fashion, first and second stimulating electrodes are threaded into the muscle at desired locations to effect contraction of the muscle around the heart upon application of electrical stimulating pulses between the two electrodes. Stimulating pulses having suitable parameters chosen to effect the desired functional contraction of the muscle are generated in synchrony with natural or stimulated heart contractions. The heart contractions are sensed by suitable sensors which apply a trigger signal to the pulse generator which responds by applying the muscle stimulating pulses to the electrodes after a predetermined time delay.

The leads are provided with electrode surface areas which can be varied at the time of surgical implantation to reflect the desired length of exposed electrode surface area extending through the muscle. Preferably the electrode is fashioned of a length of coiled wire conductor which is covered by an axially movable tubular insulating sheath. At implantation, the tubular insulation sheath may be extended over or retracted the coiled wire conductor to expose a desired length of the conductor.

30 Claims, 5 Drawing Sheets

OTHER PUBLICATIONS

"Myocardial Substitution with a Stimulated Skeletal Muscle: First Successful Clinical Case", A. Carpentier, J. C. Chachques, Letter to the Editor, The Lancet, vol. I, No. 8440, Jun. 1, 1985.

"Cardiac Assist and Myocardial Repair with Synchronously Stimulated Skeletal Muscle", Davis C. Drinkwater, Jr., M.D., Ray C. J. Chiu, M.D., et al., Am. Col. of Surgeons, Surg, Forum, vol. 31, 1980, pp. 271–274.

"Electrophysiological Conditioning of Latissimus Dorsi Muscular Flat for Myocardial Assistance", J. C. Chachques, P.A. Grandjean et al., Artificial Organs, vol. 9(A), Oct. 1985.

Brochure, "Medtronic's Model 6400 Temporary, Epicardial Pacing Lead; In Either Cardiac Chamber, It's Safe, Simple and Sure", 1982, (4 pages).

"Synchronously Stimulated Skeletal Muscle Powered Cardiac Assist: Clinical Implications" R. C.-J. Chiu, M.D., Ph.D., I. R. Neilson, M.D., A. S. Khalafalla et al.

METHOD AND APPARATUS INCLUDING A SLIDING INSULATION LEAD FOR CARDIAC ASSISTANCE

BACKGROUND OF THE INVENTION

1. Field of the Invention

This invention relates generally to a method and apparatus for muscle stimulation in the field of Functional Electrical Stimulation (FES) employing one or more adjustable surface area, electrode intramuscular lead. Potential appications are: scoliosis correction, upper and lower limb stimulation of hemi, para and quadriplegics, foot drop, respiratory support by diaphragm pacing and cardiac assistance. The particular application is reconstructive cardiac surgery for augmentation of cardiac output, and more particularly to such a method or apparatus wherein a muscle surgically implaced about the heart is electrically stimulated in synchrony with detected natural heartbeats to contract about the chambers of the heart and increase cardiac output.

2. Related Art

In recent years, a considerable amount of interest has been generated by the widespread use of cardiac stimulators and other muscle stimulators in the body to counter the effects of disease or injury which have left such muscles unable to perform satisfactorily. FES, e.g. cardiac pacing to increase cardiac output through the substitution of a higher, but physiological, heartbeat rate for that provided by the diseased or damaged heart itself, is widely known. Cardiac pacing cannot in itself replace or cure a failing heart, and for that reason natural heart transplants and artificial heart implants have become increasingly common.

In an effort to avoid the limitations of these procedures, several investigators have considered the possibility of increasing cardiac output of the patient's own failing heart by substituting body muscle for myocardial tissue and to attempt to train that muscle to operate in the same way as myocardial tissue.

The paper entitled "Functional Adaptation in Skeletal Muscle" by S. Salmons (in *Trends in Neuroscience*, 3:134–137 1980) describes the physiological differences between untrained and trained skeletal muscle.

In the paper entitled "Experimental Cardioplasty Using the Latissimus Dorsi Muscle Flap" by Juan C. Chachques, M.D. et al (in the *Journal of Cardiovascular Surgery*, 26 (5):457–462, 1985), the authors describe the procedure by which a pedicled Latissimus Dorsi flap is grafted directly to the heart in order to replace diseased or injured myocardial tissue. In the later paper entitled, "Development of a Non-tiring Stimulation of the Latissimus Dorsi Flap as a Myocardial Substitute" by J. C. Chachques et al, in *Artificial Organs*, 8:379–380, 1984, the authors describe the application of stimulating energy to the pedicled Latissimus Dorsi flap to train the muscle to contract at a frequency up to 80 beats per minute without encountering fatigue. Such a suitable trained muscle could be substituted for myocardial tissue.

The paper entitled "Synchronously Stimulated Skeletal Muscle Graft for Myocardial Repair" (in *The Journal of Thoracic and Cardiovascular Surgery*, 87 (3):325–331, 1984) describes an external system for training and stimulating a skeletal muscle cardiac graft in 1:1, 1:2 or 1:3 synchrony to detected R waves. The co-pending Medtronic U.S. patent application Ser. No. 761,252 filed Aug. 1, 1985 describes a skeletal muscle—aortic balloon system for augmenting cardiac output in synchrony with detected R waves.

In the Medtronic U.S. Pat. No. 4,411,268, a pulse generator is described for providing both conditioning and stimulating pulses to a cardiac muscle graft in synchrony with either the delivery of a stimulating pulse to the heart itself by an artificial cardiac pacemaker or in response to the sensing of a natural underlying heartbeat within the heart.

These prior systems would employ sensing in pacing electrodes within the heart and undefined electrodes applied to or extending through the muscle tissue surgically implaced around the heart or the balloon. The prior art does not appear to disclose a suitable electrode configuration for applying the muscle stimulator output pulses to the muscle itself.

BRIEF SUMMARY OF THE INVENTION

The method and apparatus of the present invention provides a system for inducing the desired functional contraction in muscle tissue employing one or more adjustable surface area, intramuscular lead(s) for applying stimulating pulses to the muscle.

The system generally comprises pulse generating means for generating suitable stimulating pulses for contracting the muscle, electrode means for electrically connecting the stimulating means to the muscle, and means for initiating the stimulating pulses in a desired stimulating regimen. The lead generally comprises lead means having a proximal and distal end carrying electrode means in the form of a length of exposed electrical conductor at the distal end of the lead means for insertion into the muscle tissue to be stimulating, and adjustable insulating means adapted to be advanced distally to electrically insulate any portion of the exposed electrical conductor which is not advanced into said muscle tissue, whereby said electrode may be adapted to the dimensions of the muscle being stimulated.

The lead and electrode are surgically placed by advancing at least a portion of the exposed electrode into muscle tissue, advancing the adjustable insulating means distally to cover and electrically insulate any exposed portion of the elongated electrode and fixedly securing the adjustable insulating means to the lead body to retain it in the advanced position.

More particularly, the system is preferably designed for functional electrical stimulation of a cardiac assist muscle graft in synchrony with the contraction of a heart to augment and strengthen the heart and comprises pulse generating means for providing stimulating pulse trains sufficient to effect the desired contraction of the muscle, sensing means for sensing natural or paced heart depolarizations and providing a synchronization signal in response thereto, first lead means coupled to the heart and to the sensing means for applying the heart signals to the sensing means, delay means responsive to the synchronization signal for developing a trigger signal after a predetermined delay period, pulse generator output stage means responsive to the trigger signal for providing the pulse train at the muscle output terminals, and second lead means coupled to the muscle stimulating output terminals and to the muscle tissue grafted to the heart for conducting the muscle stimulation pulse trains to the muscle to cause it to contract in synchrony with the sensed heart signals.

The intramuscular lead preferably further comprises a first length of conductor having a proximal end and a distal end, insulating means for electrically insulating the first length of conductor, connector means fixedly attached to said proximal end of the first length of conductor for electrically coupling the lead to the pulse generator, an electrode comprising a second length of conductor having a proximal and distal end, means for fixedly attaching the proximal end of the second length of conductor to the distal end of the first length of conductor, means fixedly attached to the distal end of the second length of conductor for inserting at least a portion of the second length of conductor into muscle tissue, and insulating sleeve means having a proximal end, a distal end and a predetermined length, the sleeve means surrounding the lead and slidable between at least the proximal and distal ends of the second length of electrical conductor whereby the insulating sleeve means may be advanced distally to overlie and electrically insulate any remaining portion of the second length of electrical conductor not positioned within muscle tissue.

The preferred method for effecting cardiac assist to a weakened heart further comprises the steps of surgically resecting an intact muscle and surgically wrapping it about the weakened heart muscle, fixing one or more electrodes each comprising a length of exposed electrical conductor to one or more separate locations in the resected muscle tissue, detecting natural heart polarizations and providing a synchronization signal in response thereto, generating a muscle stimulating pulse train after a suitable delay from the generation of the synchronization signal, and applying the muscle stimulation pulse train to each electrode to effect a contraction of the resected muscle around the weakened heart muscle in synchrony with a natural or stimulated heart depolarization to thereby increase cardiac output.

The step of placing one or more electrodes in the muscle tissue further comprises the steps of, in each instance, advancing at least a portion of the exposed electrode into muscle tissue, advancing a tubular insulating sheath distally to cover and electrically insulate any exposed portion of the elongated electrode, and fixedly securing the sheath to the lead body to retain it in the advanced position.

Finally, the method and apparatus further provides for a mesurement of the length of electrode within the muscle. The lead further comprises a first marker along the length of the lead body and a second marker along the length of the insulating sleeve. After advancement of said insulating sleeve to cover the remaining portion of the electrode not inserted within the muscle, one may measure the distance between the first and second markers to determine the length of the portion of the exposed electrical conductor inserted within the muscle tissue. This will provide the physician with an indication of exposed electrode surface area and its effect on longevity of the batteries powering the pulse generator, and the effectiveness of muscle contraction may be estimated.

BRIEF DESCRIPTION OF THE DRAWINGS

Additional objects and features of the present invention will become readily apparent when the same are set forth in greater detail in the accompanying detailed of the preferred embodiment with reference being made to the drawings in which like reference numerals represent like or similar parts throughout and in which.

DETAILED DESCRIPTION OF THE INVENTION

Figure 1:
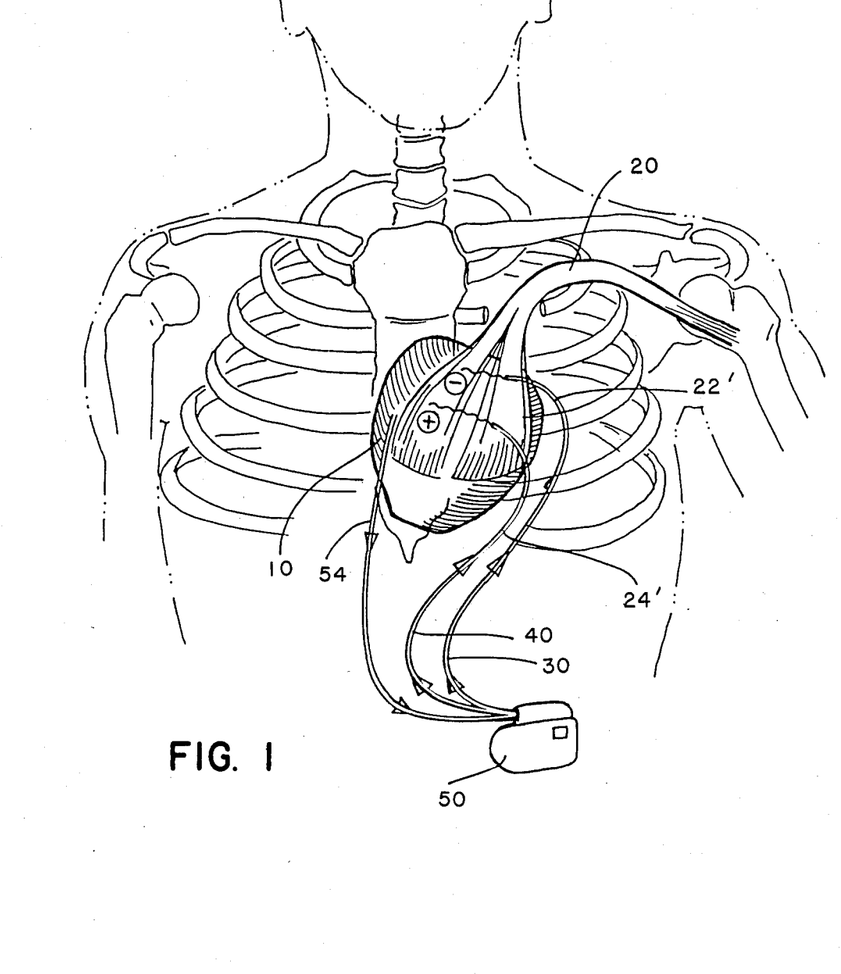
FIG. 1 is a schematic diagram of the surgical technique for muscle graft placement about the left ventricle of a human heart.

Turning now to FIG. 1, there is shown a human torso generally showing the location of the heart and the location of the left Latissimus Dorsi muscle which has been excised from its normal location and surgically grafted about the ventricle. The heart is generally depicted as 10 and the muscle is depicted as 20. The surgical procedure involves the dissection of the left Latissimus Dorsi muscle from all of its costal, vertebral and iliac insertions while leaving intact the superior vessel and nerve pedicle. The muscle is then split vertically from the center of its free end for a distance of approximately ⅔ its length. A thoracotomy at the fifth left intercostal space with pericardiotomy employed to expose the heart.

The re-section of 3 cm of the lateral arc of the second rib permits passing the dissected flap into the thoracic cavity. The posterolateral incision can then be closed and the median sternotomy opened and extended into the epigastrium. The two ends of the flap are then fixed to both the right and left ventricles with a suitable number of separated sutures to thereby wrap around the exposed surface of the heart as shown in FIG. 1.

The muscle is then tested by electrical stimulation with a muscle stimulator to see if the stimulation causes an acceptable contraction of the ventricles of the heart 10. Preferably the muscle has, several months prior to the operation, been chronically stimulated while in situ to strengthen it to alleviate fatiguing by the repetitious stimulation at the normal frequency of the natural heartbeat. Such a muscle strengthening regimen is disclosed in the Chachques et al paper appearing in *Artificial Organs* previously referred to.

Such a surgical procedure involving the resection of a large cardiac tumor is reported in the letter "Myocardial Substitution with a Stimulated Skeletal Muscle:- First Successful Clinical Case", (in *The Lancet*, 8440:1267, June 1, 1985). This report does not reveal the design of the leads employed in that procedure.

Figure 2:
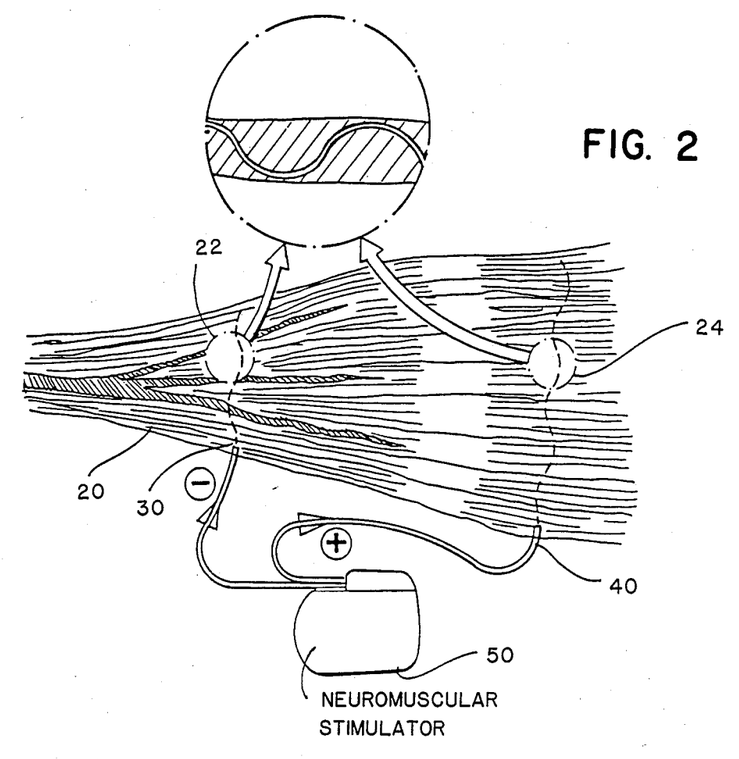
FIG. 2 is a schematic illustration of how the intramuscular lead(s) of the present invention would be threaded into the muscle to provide a variable electrode surface areas as desired.

At the time that the muscle is trained, electrodes are positioned in the muscle as very generally shown in FIG. 2. Two or more leads 30 and 40 are threaded into the muscle 20 a suitable distance apart (such as 12 cm) so that the exposed electrode surface areas lie within the muscle flap along the paths 22 and 24, respectively. A sigma like path is favourable for minimizing electrode mechanical stress. The stimulation program of the type set forth in the *Artificial Organ* article may be employed to strengthen the muscle and increase its bulk and resistance to fatigue.

At the time of the operative procedure set forth above, the stimulating leads employed in the training regimen may be removed and replaced by new leads threaded into the muscle along the paths 22' and 24' depicted in FIG. 1. Those electrodes are connected through insulated leads to a pulse generator of the type disclosed in the aforementioned U.S. Pat. No. 4,411,268 and as described in regard to FIG. 3. In this fashion, the indwelling permanent leads are expected to conduct electrical stimulation into the muscle graft so that it contracts in synchrony with detected natural heartbeats or paced beats to forcefully compress the ventricles of the heart 10 in the manner described in the '268 patent.

Figure 3:
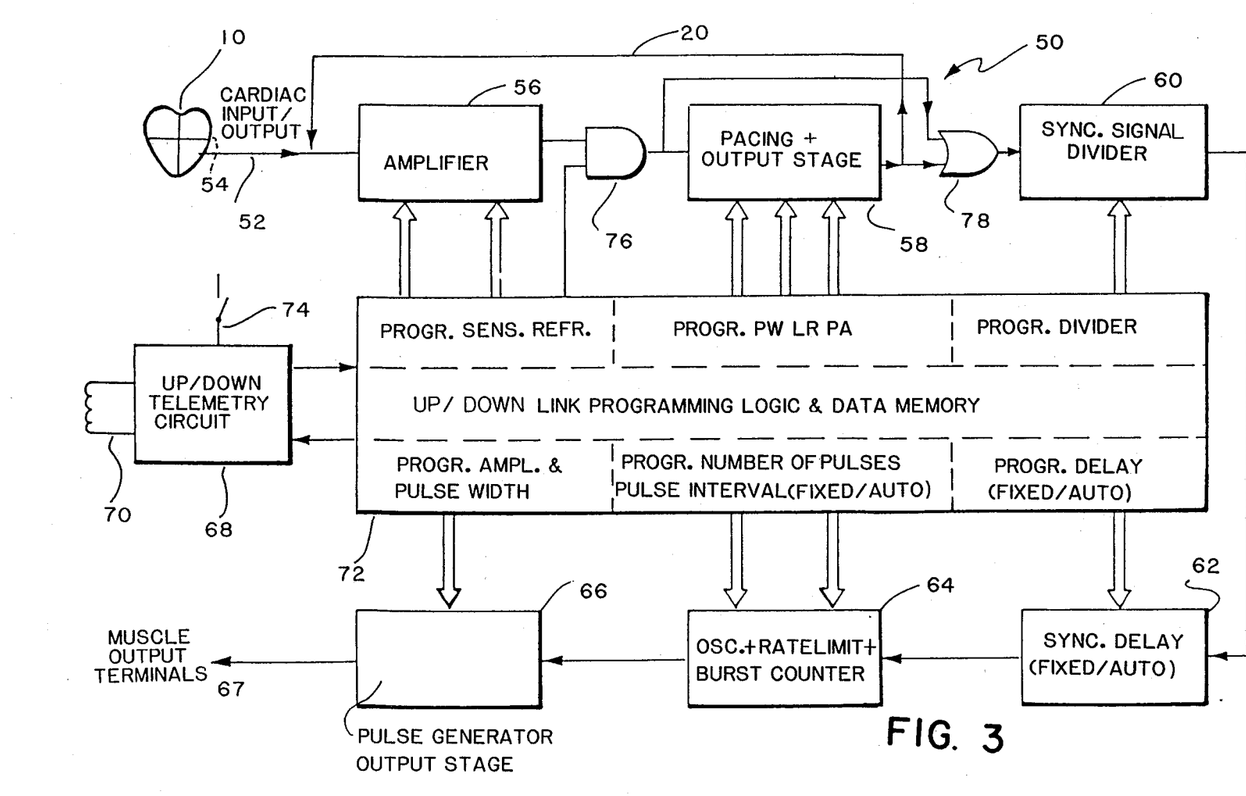
FIG. 3 is a block diagram of one form of electrical stimulator that may be used in the practice of the invention.
Figure 4:
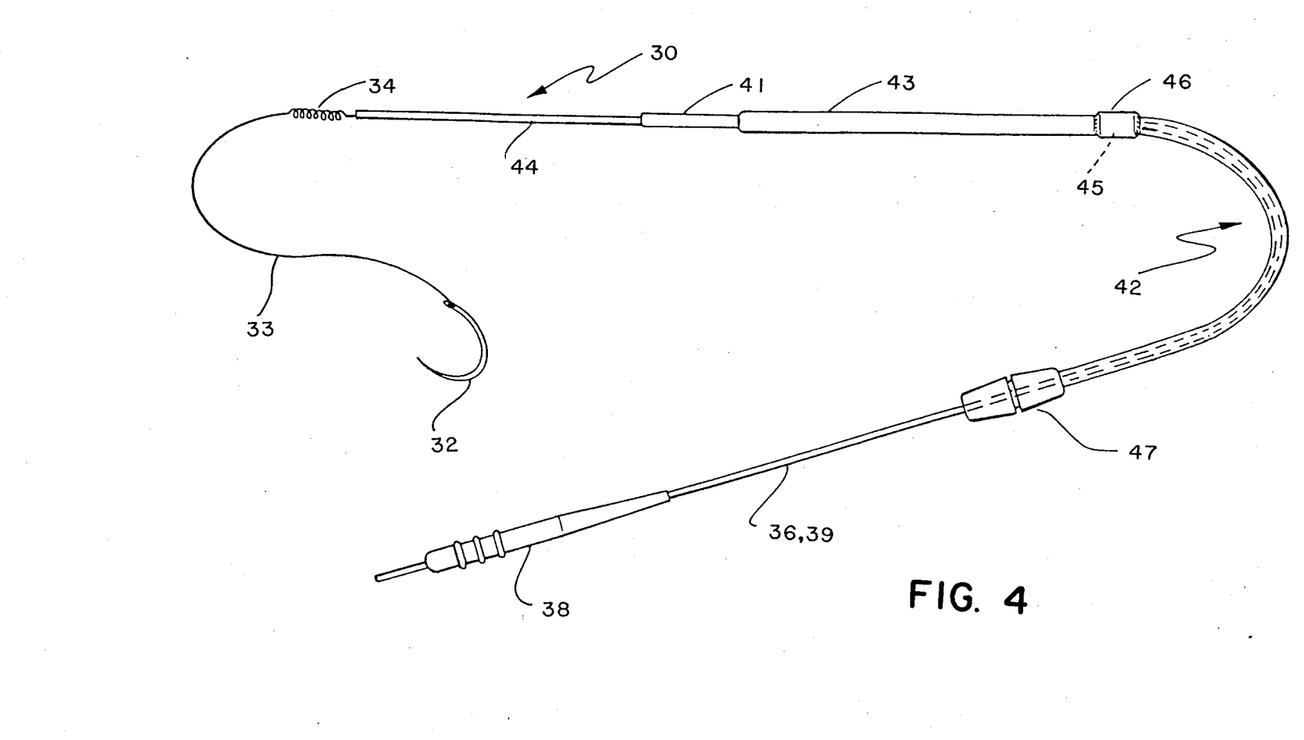
FIG. 4 is a schematic diagram of one embodiment of the intramuscular lead(s) of the present invention.
Figure 5:
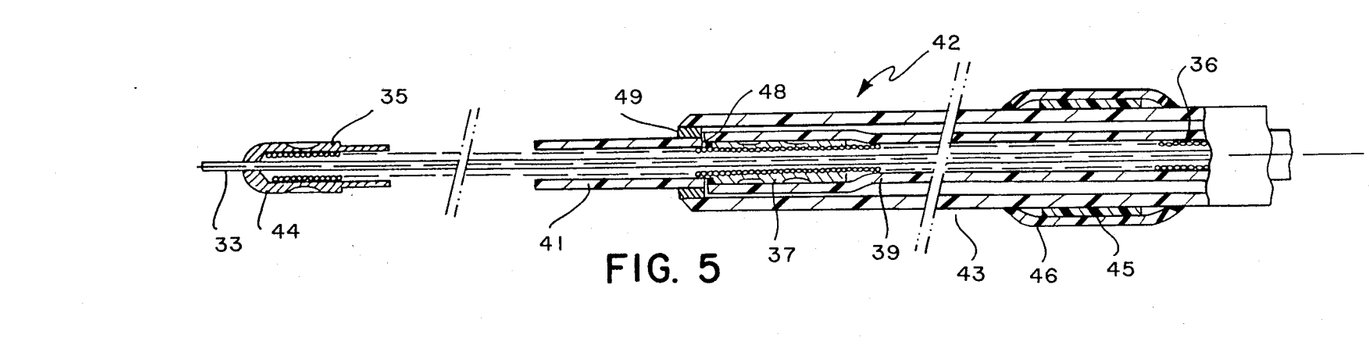
FIG. 5 is a sectional view of the lead of FIG. 3 with the electrode surface area retracted.
Figure 6:
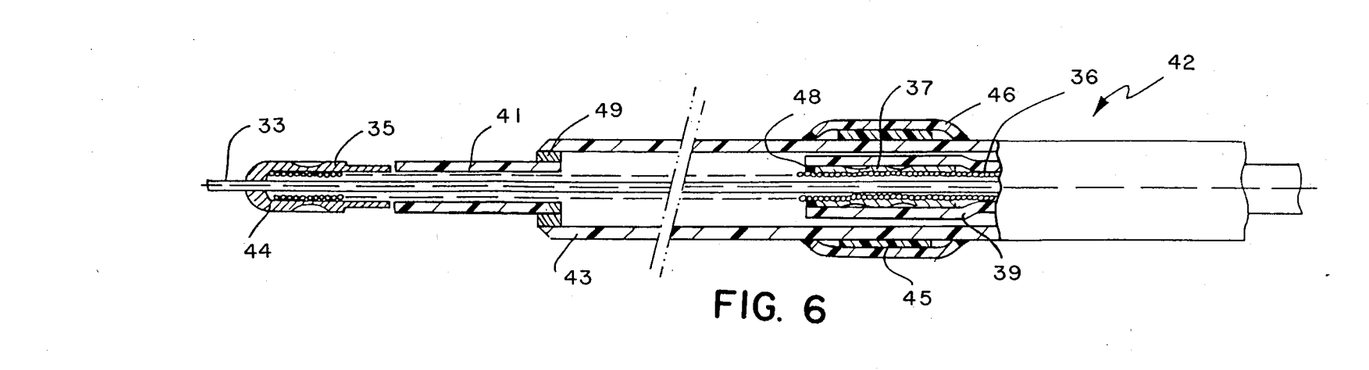
FIG. 6 is a cross-sectional view of the distal end of the lead of FIG. 3 showing how the electrode surface area exposed.

Turning now to the preferred embodiment of the pulse generator and lead of the present invention, FIG. 3 depicts in block diagram form a programmable cardiac pacemaker and muscle stimulator and FIGS. 4–6 depict the lead. A cardiac pacing lead 54 is further depicted in FIG. 1 for carrying natural heart signals and pacing stimuli between the heart 10 and the pulse generator 50 in a manner described hereafter.

In FIG. 3, the pulse generator 50 is coupled to its input terminal 52 and the cardiac pacing lead 54 to the heart 10 and at its muscle output terminals to two or more leads attached to the muscle 20. The pulse generator comprises a pacing sense amplifier 56, a pacing output stage 58, a sync signal divider 60, sync delay 62, oscillator, rate limit and burst counter 64, pulse generator output stage 66, an up-down telemtry circuit 68 and antenna 70, and programmable memory and logic 72 along with magnetically activated switch 74 and gates 76 and 78. Very generally, the amplifier 56, pacing output stage 58, up-down telemetry circuit 68, 70 and 74 and certain of the programmable logic and memory within block 72 are preferrably derived from the Medtronic ® SYMBIOS ® Model 7005/6 DDD pacemaker and the lead 54 may be any conventional myocardial or transvenous pacing lead. The oscillator and rate limit and burst counter 64 and output stage 66 together with certain of the programmable memory and logic circuitry within block 72 may be derived from the Medtronic ® Itrel ® Model 7420 implantable muscle stimulator. The remaining blocks 60 and 62 together with their associated portions of the memory and logic block 72 are specially designed to apply the sensed or paced output of the pacing stage after a suitable programmable delay to trigger the muscle stimulator stages into producing the suitable burst of stimuli to the Latissimus Dorsi muscle 20.

In regard to the pacing portion of FIG. 3, the sense amplifier 56 has a programmable sensitivity and refractory interval established by the data stored in memory in the block 72. If it detects a suitable heartbeat, it produces a trigger signal which is passed through the AND gate 76 to both the pacing output stage 58 and to the sync signal divider 60 through OR gate 78. The pacing output stage 58 may be programmed to be operative or inoperative, depending upon whether or not the patient's natural heartbeat recurs at satisfactory rates and/or whether or not the physician prefers to pace at a fixed rate or in synchrony to the patient's natural heart rate. In the event that the patient's underlying rate falls below the programmed lower rate of the pacemaker, then the pacing impulse will be triggered and applied through conductor 80, connector 52 and lead 54 to the patient's heart and separately through OR gate 78 to the sync signal divider 60. The pulse width lower rate and pulse amplitude of the pacing output stimuli are set in accordance with the programmed memory within the block 72.

The signal applied through OR gate 78 is applied to trigger signal divider 60 which may be programmed to a 1:1, 1:2 or 1:N division ratio in accordance with the ratio established in the programmable divider memory portion of the block 72. The sync signal divider 60 may furthermore be made operational when the natural sensed heartbeat exceeds a certain upper rate. Alternatively the refractory interval of the amplifier 56 may be set to an interval that provides an effective upper rate limit for sensed heart signals. In either case, the purpose of the 1:2, 1:N division is to avoid stimulating the muscle 20 at such a high repetition rate that it fatigues. Even though the muscle may be trained and subsequently conditioned in the manner described in the aforementioned U.S. Pat. No. 4,411,268, it may still be fatigued at high repetition rates.

The sync signal is then applied to the input of the synch delay circuit 62 which after a programmable delay applies a sync signal to the oscillator and rate limit burst counter 64. The delay interval is set by the delay interval programmed into the program delay memory stages of block 72.

The oscillator and rate limit and burst counter 64 provides a predetermined programmed number of trigger pulses each separated by a programmed interval to the input of the pulse generator output stage 66. The number of pulses and the pulse interval are controlled by the data stored in the programmable number of pulses and pulse interval memory portion of block 72.

The pulse generator output stage 66 responds to the programmable number of pulses in the burst of trigger pulses received from block 64 by providing a like numbered burst of muscle stimulating output pulses each having a programmed amplitude and pulse width and each separated by the programmed pulse interval. Again, the amplitude and pulse width of each of the muscle stimulating pulses in the burst is controlled by programmable amplitude and pulse width value stored in memory in block 72.

In general terms, the pulse generator of FIG. 3 operates in similar fashion to that disclosed in the aforementioned '268 patent and provides bursts of muscle stimulator pulses similar to those disclosed in the aforementioned Dewar et al article. The specifications of the pulse generator of FIG. 3 are as follows:

| Ventricular channel: (all programmable) | unipolar sense/pace<br>sensitivity: .75, 1.5, 3.0 mV<br>pace pulse amplitude: 5.5 V ± .3 V<br>pace pulse width: 0.05–1.5 ms<br>(steps of 0.5 ma)<br>lower rate: 30–120 ppm<br>trigger delay: 6–250 ms<br>(steps of 4 ms)<br>refractory period: 200–300–400 ms<br>(excluding trigger delay) |
|---|---|
| Muscle channel: (all programmable) | on/off<br>bipolar (pace only)<br>burst lengths: 150 & 250 ms<br>pulse width: .05–1.5 ms<br>(steps of .05 ms)<br>pulse amplitude: .25 V–10.5 V<br>(steps of .25 V)<br>burst rate: 1–256 Hz<br>2 synchronization modes 1:1 & 1:2<br>upper rate: |

| Telemetry (optional by means of special programmer) | 100 bpm in 1:1 mode
50 bpm in 1:2 mode
marker channel indicator
ventricular sense
ventricular sense within refractory period
ventricular pace
delayed trigger pulse |
|---|---|

Synchronization Modes

The synchronization QRS—muscle pacing will depend on two parameters:
 (a) the selected synchronization mode;
 (b) the heart rate
as shown in the following table for two different designs. One design will be selected.

| Selected Mode | Effective Mode | |
|---|---|---|
| | HR < 100 ppm | HR > 100 ppm |
| 1:1 | 1:1 | 1:2 |
| 1:2 | 1:2 | 1:4 |

Turning now to FIGS. 4-6, there is shown a schematic representation of one of the intramuscular leads 30 or 40 adapted to be coupled to the output stage 66 of the pulse generator 50 of FIG. 3. Very generally, the lead 30 comprises a suture needle 32 which is adapted to be drawn through the muscle 20, a length of non-conductive line 33 having a coil 34, a lead body 36 and connector 38 with a slidable insulating tube or sheath 42 lying over a portion of the insulated conductor 36 and the exposed electrode 44. The connector 38 is adapted to be coupled to one of the output terminals 67 of FIG. 3 after the electrode 44 at the distal end of the lead has been drawn through the muscle 20 at an appropriate location. Before implanting the electrode into the muscle, the electrode surface is fully exposed by sliding the tubing sheath 42 towards the connector 38 by holding the distal end of the electrode 44 and pulling the suture ring 47 proximally. After placing the electrode in the muscle, needle 32 and length of line 33 are severed at the distal end of the coil 34. The coil 34 is designed to retain the electrode in position within the muscle in the manner in which a similar coil operates in the Medtronic Model 6400 heart wire. A length of the line 33 may alternately be employed to fix the electrode by tying or clipping it to the muscle.

The portion of the electrode 44 left exposed may be adjusted by sliding the tubing 42 axially over the insulating sleeve 36 and exposed electrode 44 in a direction away from the connector 38 until the distal end of sleeve 41 reaches the muscle surface. In FIG. 4, the insulating tubing 42 is shown completely exposing the electrode 44. The insulating sheath means 42 contains a reduced diameter portion 41 and an expanded diameter portion 43 together with an exterior marker 45 and suture sleeve 47. The interior marker 48 adjoins the insulating sleeve 36 at its distal end.

As the sliding tubing 42 is withdrawn proximally, the conductive electrode 44 is exposed. The exposed length is indicated by the distance between the exterior marker 45 and the interior marker 48. In order to increase the stimulating electrode length, the slidable tubing is grasped at the suture sleeve 47 and pulled gently proximally. To decrease the stimulating electrode length, the insulating tubing 42 is grasped at the holder 46 and at the connector 38 and advanced distally. The distal portion of the lead 30 of FIG. 4 is shown in an expanded cross-section with the insulating sleeve 42 retracted in FIG. 5 and extended in FIG. 6.

The electrode 44 shown in FIGS. 5 and 6 comprises a length of coiled wire conductor 44 extending between the distal terminal 35 and the swaging ring 37. The insulated conductor 36 extends between the ring 37 and the connector 38. The coiled wire conductor for the electrode 44 may consist of platinum iridium or other electrode materials, whereas the lead conductor 36 may consist of MP35N or other suitable lead materials. The lead conductor 36 and sleeve 37 are insulated by an insulating tube or covering 39 which extends from the distal end 48 of the sleeve 37 back to the connector 38.

The reduced diameter sleeve portion 41 is joined to the larger diameter sleeve portion 43 by ring 49 to form the adjustable sleeve means 42.

The distal end of swaging ring 39 constitutes one marker 48 of the exposed length marker and the tube 45 on sleeve 43 constitutes the other marker. The line or suture material 33 extends through the lumen of the coiled wire conductors 44 and 36 back to the connector 38 for added strength.

Although the marker 48 is shown at the distal end of sleeve 37, sleeve 37 may itself serve as the marker 48, since the insulating sleeves 42 and 39 are generally transparent.

In use, the electrode 44 is shown in its extended position in FIG. 5 in its retracted position in FIG. 6. As stated before, one may determine the length of electrode conductor within the muscle by observing the distance between the markers 45 and 48, 37 which are observable through the transparent insulating sheaths 39 and 43. As shown in FIG. 6, markers 45 and 48 (including 37) overlie one another when the electrode 44 is fully insulated.

The ring 49 is a suturing ring to fix the insulating sleeve 43 to covering 39. The visual marker 45 is, in this configuration, a piece of white Teflon ® tubing that is kept in place by a transparent cover sleeve 46. This marker could also be of another design such as an ink spot or ring, or could be made of a radio opaque material for X-ray check-up.

Knowledge of the exposed electrode length is useful to the surgeon:
 1. to optimize electrode location;
 2. to make sure that electrode area is sufficient with respect to electrical energy required for the application (in order to obviate electrochemical problems);
 3. if a highly specific stimulation is required and if two similar intramuscular electrodes are used, it is useful to reduce the cathodic electrode area to a minimum in order to increase its current density and to maximize anode surface. It is useful to estimate these surface or exposed lengths during surgery; and
 4. once implanted into the muscle, it is difficult to estimate the length exposed. It reassures the surgeon to have an indication about electrode area (or length) especially when surgery becomes a routine.

Future generations of the system will aim at providing full management of heart conduction problems (bradycardia, tachycardia, fibrillation, etc.) as well as providing optimal cardiac output by appropriate muscle stimulation. This latter function could be carried out, for instance, by closed-loop synchronous pacing of muscle(s) regulated by patient's activity, heart rate, stroke volume, cardiac output, etc. These sensor inputs could direct the best appropriate muscle/heart complex stimulation scheme (e.g., synchronization delay, pulse width and/or amplitude and/or frequency and/or burst duration modulations, etc.) via the most appropriate electrode(s) (if multichannel stimulation is used).

Many other modifications and variations of the present invention are possible in light of the above teachings. While the intramuscular lead is described in conjunction with reconstructive cardiac surgery and a pulse generator for effecting stimulating of the muscle in synchrony with paced or sensed cardiac events, the lead could be also used for stimulation of various other muscles for other applications of functional electrical stimulation. It is therefore to be understood that, within the scope of the appended claims, the invention may be practiced otherwise than as specifically described.

Sensors could also be provided to detect and/or prevent muscle fatigue and therefore ensure the patient with an optimal long term cardiac output. Means could also be provided to enable distant monitoring of patient well being (e.g., by telephone) and of cardio-myostimulator status as can be currently done with cardiac pacemakers.

The system as described has been originally designed for providing cardiac assistance by pacing the Latissimus Dorsi muscle wrapped around the heart. Leads as well as cardio-myostimulator characteristics make such a system suitable for applications where other skeletal muscle must be substituted for the Latissimus Dorsi muscle and paced in synchrony with heart contractions.

What is claimed is:

1. A lead for establishing electrical contact between body tissue and a medical device comprising:
    a first length of conductor having a proximal end and a distal end;
    insulating means for electrically insulating said first length of conductor;
    connector means fixedly attached to said proximal end of said first length of conductor for electrically coupling said lead to a medical device;
    an electrode comprising a second length of conductor having a proximal and distal end;
    means for fixedly attaching the proximal end of said second length of conductor to the distal end of said first length of conductor;
    means fixedly attached to the distal end of said second length of conductor for inserting at least a portion of said second length of conductor into muscle tissue; and
    insulating sleeve means having a proximal end, a distal end and a predetermined length, said sleeve means surrounding said lead and slidable between at least said proximal and distal ends of said second length of electrical conductor whereby said insulating sleeve means may be advanced distally to overlie and electrically insulate any remaining portion of said second length of electrical conductor not positioned within muscle tissue.

2. The lead of claim 1 wherein a first marker is fixedly attached to a first position on said lead and a second marker is fixedly attached to a second position on said slidable insulating sleeve means so that the distance between the first and second markers is generally equal to the portion of said second electrical conductor actually inserted within the muscle tissue when said sleeve means is advanced distally to electrically insulate any remaining portion of said second length of electrical conductor not within the muscle tissue.

3. The lead of claim 2 wherein:
    said first length of electrical conductor and insulating sheath means has a first outside diameter and said second length of exposed electrical conductor has a second outer diameter;
    and wherein said slidable insulating sleeve means further comprises:
    a first length of tubular insulating sleeve material having a first lumen having an inner diameter large enough to receive the said first outer diameter;
    a second length of tubular insulating sleeve material having a second lumen having an inside diameter large enough to accommodate said second length of electrical conductor, said inside diameter of said second lumen being too small to accommodate and slide over said first length of insulated electrical conductor; and
    means for joining said first and second sleeves together whereby said insulating sleeve means may be advanced distally to insulate a portion or all of said second length of electrical conductor and retracted proximally until said second length of insulating sleeve means abuts the distal end of said electrical insulating coating.

4. The lead of claim 3 wherein said joining means comprises said second marker.

5. The lead of claim 1 wherein:
    said first length of electrical conductor and insulating sheath means has a first outside diameter and said second length of exposed electrical conductor has a second outer diameter;
    and wherein said slidable insulating sleeve means further comprises:
    a first length of tubular insulating sleeve material having a first lumen having an inner diameter large enough to receive the said first outer diameter;
    a second length of tubular insulating sleeve material having a second lumen having an inside diameter large enough to accommodate said second length of electrical conductor, said inside diameter of said second lumen being too small to accommodate and slide over said first length of insulated electrical conductor; and
    means for joining said first and second sleeves together whereby said insulating sleeve means may be advanced distally to insulate a portion or all of said second length of electrical conductor and retracted proximally until said second length of insulating sleeve means abuts the distal end of said electrical insulating coating.

6. The lead of claim 1 wherein said attachment means further comprises:
    a length of surgical line having a proximal end and a distal end wherein said proximal end of said line is fixedly attached to said distal end of said second length of electrical conductor comprising said electrode;
    a needle fixedly attached to said distal end of said line; and
    means fixedly attached to said line for frictionally resisting the movement of said surgical thread relative to said muscle tissue.

7. A method of electrode placement for use in the electrical stimulating of muscle tissue, said electrode comprising a length of exposed electrical conductor at the distal portion of an otherwise insulated lead comprising the steps of:
- advancing at least a portion of said exposed electrode into muscle tissue;
- advancing a tubular insulating sheath distally to cover and electrically insulate any exposed portion of said elongated electrode; and
- fixedly securing said sheath to said lead body to retain it in the advanced position.

8. The method of claim 7 wherein said lead further comprises a first marker along the length of said lead body and a second marker along the length of said insulating sleeve and further comprising the steps of:
- measuring the distance between said first and second markers to determine the length of the portion of the exposed electrical conductor inserted within the muscle tissue after advancement of said insulating sleeve to cover the remaining portion of said electrode not inserted within said muscle.

9. The method of claim 7 further comprising the step of fixing said electrode within said muscle tissue to prevent its retraction.

10. The method of claim 9 wherein said step of inserting the portion of the distal electrode into muscle tissue further comprises the steps of:
- inserting a needle through the muscle in the desired path of the portion of electrode;
- drawing the electrode through the muscle in the path of the needle;
- mechanically fixing the portion of the electrode drawn into the muscle in place to avoid retraction; and
- removing the needle.

11. The method of claim 10 wherein said lead further comprises a first marker along the length of said lead body and a second marker along the length of said insulating sleeve and further comprising the steps of:
- measuring the distance between said first and second markers to determine the length of the portion of the exposed electrical conductor inserted within the muscle tissue after advancement of said insulating sleeve to cover the remaining portion of said electrode not inserted within said muscle.

12. In a system for stimulating a muscle comprising pulse generating means for generating suitable stimulating pulses for contracting the muscle, electrode means for electrically connecting the stimulating means to the muscle, and means for initiating the stimulating pulses in a desired stimulating regimen the improvement comprising:
- lead means having a proximal and distal end carrying said electrode means in the form of a length of exposed electrical conductor at the distal end of said lead means for insertion into the muscle tissue to be stimulated, and;
- adjustable insulating means adapted to be advanced distally to electrically insulate any portion of said length of electrical conductor which is not advanced into said muscle tissue, whereby said electrode may be adapted to the dimensions of the muscle being stimulated.

13. The system of claim 12 wherein said lead means further comprises:
- a first length of conductor having a proximal end and a distal end;
- insulating means for electrically insulating said first length of conductor; and
- connector means fixedly attached to said proximal end of said first length of conductor for electrically coupling said lead to a medical device;

said electrode means further comprises:
- an electrode comprising a second length of conductor having a proximal and distal end;
- means for fixedly attaching the proximal end of said second length of conductor to the distal end of said first length of conductor; and
- means fixedly attached to the distal end of said second length of conductor for inserting at least a portion of said second length of conductor into muscle tissue; and wherein said adjustable insulating means further comprises:
- an insulating sleeve means having a proximal end, a distal end and a predetermined length, said sleeve means surrounding said lead and slidable between at least said proximal and distal ends of said second length of electrical conductor whereby said insulating sleeve means may be advanced distally to overlie and electrically insulate any remaining portion of said second length of electrical conductor not positioned within muscle tissue.

14. The lead claim 13 wherein a first marker is fixedly attached to a first position on said lead and a second marker is fixedly attached to a second position on said slidable insulating sleeve means so that the distance between the first and second markers is generally equal to the portion of said second electrical conductor actually inserted within the muscle tissue when said sleeve means is advanced distally to electrically insulate any remaining portion of said second length of electrical conductor not within the muscle tissue.

15. The lead of claim 13 wherein:
- said first length of electrical conductor and insulating sheath means has a first outside diameter and a said second length of exposed electrical conductor has a second outer diameter;
- and wherein said slidable insulating sleeve means further comprises:
  - a first length of tubular insulating sleeve material having a first lumen having an inner diameter large enough to receive the said first outer diameter;
  - a second length of tubular insulating sleeve material having a second lumen having an inside diameter large enough to accommodate said second length of electrical conductor, said inside diameter of said second lumen being too small to accommodate and slide over said first length of insulated electrical conductor;
  - means for joining said first and second sleeves together whereby said insulating sleeve means may be advanced distally to insulate a portion or all of said second length of electrical conductor and retracted proximally until said second length of insulating sleeve means abuts the distal end of said electrical insulating coating.

16. The lead claim 15 wherein a first marker is fixedly attached to a first position on said lead and a second marker is fixedly attached to a second position on said slidable insulating sleeve means so that the distance between the first and second markers is generally equal to the portion of said second electrical conductor actually inserted within the muscle tissue when said sleeve means is advanced distally to electrically insulate any remaining portion of said second length of electrical conductor not within the muscle tissue.

17. The lead of claim 13 wherein said attachment means further comprises:
- a length of surgical line having a proximal end and a distal end wherein said proximal end of said line is fixedly attached to said distal end of said second length of electrical conductor comprising said electrode;
- a needle fixedly attached to said distal end of said line; and
- means fixedly attached to said line for frictionally resisting the movement of said surgical thread relative to said muscle tissue.

18. A system for functional electrical stimulation of a cardiac assist muscle graft in synchrony with the contraction of a heart to augment and strengthen the heart comprising:
- pulse generating means for providing stimulating pulse trains sufficient to effect a desired contraction of the muscle;
- sensing means for sensing natural heart depolarizations and providing a synchronization signal in response thereto;
- first lead means coupled to said heart and to said sensing means for applying said heart signals to said sensing means;
- delay means responsive to said synchronization signal for developing a trigger signal after a predetermined delay period;
- pulse generator output stage means responsive to said trigger signal for providing said pulse train at said muscle output terminals; and
- second lead means coupled to said muscle stimulating output terminals and to said muscle tissue grafted to said heart for conducting said muscle stimulation pulse trains to said muscle to cause it to contract in synchrony with said sensed heart signals, said second lead means further comprising:
  - lead means having a proximal and distal end carrying said electrode means in the form of a length of exposed electrical conductor at the distal end of said lead means for insertion into the muscle tissue to be stimulated, and;
  - adjustable insulating means adapted to be advanced distally to electrically insulate any portion of said length of electrical conductor which is not advanced into said muscle tissue, whereby said electrode may be adapted to the dimensions of the muscle being stimulated.

19. The system of claim 18 wherein said lead means further comprises:
- a first length of conductor having a proximal end and a distal end;
- insulating means for electrically insulating said first length of conductor; and
- connector means fixedly attached to said proximal end of said first length of conductor for electrically coupling said lead to a medical device;
- said electrode means further comprises:
  - an electrode comprising a second length of conductor having a proximal and distal end;
  - means for fixedly attaching the proximal end of said second length of conductor to the distal end of said first length of conductor; and
  - means fixedly attached to the distal end of said second length of conductor for inserting at least a portion of said second length of conductor into muscle tissue; and
- wherein said adjustable insulating means further comprises:
  - an insulating sleeve means having a proximal end, a distal end and a predetermined length, said sleeve means surrounding said lead and slidable between at least said proximal and distal ends of said second length of electrical conductor whereby said insulating sleeve means may be advanced distally to overlie and electrically insulate any remaining portion of said second length of electrical conductor not positioned within muscle tissue.

20. The lead claim 19 wherein a first marker is fixedly attached to a first position on said lead and a second marker is fixedly attached to a second position on said slidable insulating sleeve means so that the distance between the first and second markers is generally equal to the portion of said second electrical conductor actually inserted within the muscle tissue when said sleeve means is advanced distally to electrically insulate any remaining portion of said second length of electrical conductor not within the muscle tissue.

21. The system of claim 19 wherein said pulse generating means further comprises:
- pacing signal generating means for generating a pacing stimulus in the absence of a sensed natural heart contraction after a predetermined interval and for applying said pacing stimulus through said first lead to the heart; and
- wherein said delay means is responsive to the generation of a pacing stimulus for providing said trigger signal.

22. The lead of claim 18 wherein:
said first length of electrical conductor and insulating sheath means has a first outside diameter and a said second length of exposed electrical conductor has a second outer diameter;
and wherein said slidable insulating sleeve means further comprises:
- a first length of tubular insulating sleeve material having a first lumen having an inner diameter large enough to receive the said first outer diameter;
- a second length of tubular insulating sleeve material having a second lumen having an inside diameter large enough to accommodate said second length of electrical conductor, said inside diameter of said second lumen being too small to accommodate and slide over said first length of insulated electrical conductor;
- means for joining said first and second sleeves together whereby said insulating sleeve means may be advanced distally to insulate a portion or all of said second length of electrical conductor and retracted proximally until said second length of insulating sleeve means abuts the distal end of said electrical insulating coating.

23. The lead claim 22 wherein a first marker is fixedly attached to a first position on said lead and a second marker is fixedly attached to a second position on said slidable insulating sleeve means so that the distance between the first and second markers is generally equal to the portion of said second electrical conductor actually inserted within the muscle tissue when said sleeve means is advanced distally to electrically insulate any remaining portion of said second length of electrical conductor not within the muscle tissue.

24. The lead of claim 18 wherein said attachment means further comprises:
- a length of surgical line having a proximal end and a distal end wherein said proximal end of said line is fixedly attached to said distal end of said second length of electrical conductor comprising said electrode;
- a needle fixedly attached to said distal end of said line; and
- means fixedly attached to said line for frictionally resisting the movement of said surgical thread relative to said muscle tissue.

25. The system of claim 18 wherein said pulse generating means further comprises:
- pacing signal generating means for generating a pacing stimulus in the absence of a sensed natural heart contraction after a predetermined interval and for applying said pacing stimulus through said first lead to the heart; and
- wherein said delay means is responsive to the generation of a pacing stimulus for providing said trigger signal.

26. A method for effecting a cardiac assist to a weakened heart comprising the steps of:
- surgically resecting an intact muscle and surgically placing it about the weakened heart muscle;
- fixing one or more electrodes each comprising a length of exposed electrical conductor to one or more separate locations in the resected muscle tissue;
- detecting natural heart polarizations and providing a synch signal in response thereto;
- generating a muscle stimulating pulse train after a suitable delay from the generation of said synch signal; and
- applying said muscle stimulation pulse train to each electrode to effect a contraction of the resected muscle around the weakened heart muscle in synchrony with a natural or stimulated heart depolarization to thereby increase cardiac output;

wherein the step of placing one or more electrodes in the muscle tissue further comprises the steps of, in each instance:
- advancing at least a portion of said exposed electrode into muscle tissue;
- advancing a tubular insulating sheath distally to cover and electrically insulate any exposed portion of said elongated electrode; and
- fixedly securing said sheath to said lead body to retain it in the advanced position.

27. The method of claim 26 wherein said lead further comprises a first marker along the length of said lead body and a second marker along the length of said insulating sleeve and further comprising the steps of:
- measuring the distance between said first and second markers to determine the length of the portion of the exposed electrical conductor inserted within the muscle tissue after advancement of said insulating sleeve to cover the remaining portion of said electrode not inserted within said muscle.

28. The method of claim 26 further comprising the step of fixing said electrode within said muscle tissue to prevent its retraction.

29. The method of claim 28 wherein said step of inserting the portion of the distal electrode into muscle tissue further comprises the steps of:
- inserting a needle through the muscle in the desired path of the portion of electrode;
- drawing the electrode through the muscle in the path of the needle;
- mechanically fixing the portion of the electrode drawn into the muscle in place to avoid retraction; and
- removing the needle.

30. The method of claim 29 wherein said lead further comprises a first marker along the length of said lead body and a second marker along the length of said insulating sleeve and further comprising the steps of:
- measuring the distance between said first and second markers to determine the length of the portion of the exposed electrical conductor inserted within the muscle tissue after advancement of said insulating sleeve to cover the remaining portion of said electrode not inserted within said muscle.

* * * * *